(12) United States Patent
Frotscher et al.

(10) Patent No.: US 11,327,039 B2
(45) Date of Patent: May 10, 2022

(54) MONITORING OF GASES PRODUCED IN AN INSULATING-MEANS CIRCUIT

(71) Applicant: Maschinenfabrik Reinhausen GmbH, Regensburg (DE)

(72) Inventors: Rainer Frotscher, Regenstauf (DE); Andreas Sachsenhauser, Mallersdorf (DE)

(73) Assignee: MASCHINENFABRIK REINHAUSEN GMBH, Regensburg (DE)

( * ) Notice: Subject to any disclaimer, the term of this patent is extended or adjusted under 35 U.S.C. 154(b) by 0 days.

(21) Appl. No.: 17/311,362

(22) PCT Filed: Dec. 5, 2019

(86) PCT No.: PCT/EP2019/083870
§ 371 (c)(1),
(2) Date: Jun. 7, 2021

(87) PCT Pub. No.: WO2020/115232
PCT Pub. Date: Jun. 11, 2020

(65) Prior Publication Data
US 2022/0026385 A1    Jan. 27, 2022

(30) Foreign Application Priority Data

Dec. 7, 2018 (DE) ............. 10 2018 131 388.8

(51) Int. Cl.
*G09G 3/3225* (2016.01)
*G09G 3/20* (2006.01)
(Continued)

(52) U.S. Cl.
CPC ............. *G01N 27/16* (2013.01); *G01N 25/30* (2013.01); *H01H 33/56* (2013.01); *H01H 2033/567* (2013.01)

(58) Field of Classification Search
CPC .......... G01N 21/3504; G01N 33/2841; G01N 29/02; G01N 29/24; G01N 33/28;
(Continued)

(56) References Cited

U.S. PATENT DOCUMENTS 8,738,301 B2 * 5/2014 Frotscher .......... G01N 33/2841
702/24
9,513,275 B2 * 12/2016 Pruente .............. G01N 33/2841
2014/0165704 A1   6/2014 Maity et al.

FOREIGN PATENT DOCUMENTS

EP           3073248 A1    9/2016
WO   WO 2007115807 A1   10/2007

OTHER PUBLICATIONS

Lin, et al., "Online Monitoring Data Cleaning of Transformer Considering Time Series Correlation," *IEEE/PES Transmission and Distribution Conference and Exposition*, Apr. 16, 2018, pp. 1-9, Institute of Electrical and Electronics Engineers, Piscataway, NJ, USA.

(Continued)

*Primary Examiner* — Brandi N Hopkins
(74) *Attorney, Agent, or Firm* — Leydig, Voit & Mayer, Ltd.

(57) ABSTRACT

A method monitors gases produced in an insulating medium circuit. The insulating medium circuit is in contact with a transition resistor of an on-load tap-changer. The method includes: ascertaining a time profile of a resistor temperature of the transition resistor during a loading time period; and determining at least one characteristic value for characterizing the gases produced based upon the time profile of the resistor temperature.

14 Claims, 2 Drawing Sheets

(51) Int. Cl.
*G01N 27/16* (2006.01)
*H01H 33/56* (2006.01)
*G01N 25/30* (2006.01)

(58) Field of Classification Search
CPC .. G01N 21/1702; G01N 33/004; G01N 33/26; G01N 21/25; G01N 2021/1704; G01J 3/0235; G01J 3/42
See application file for complete search history.

(56) References Cited

OTHER PUBLICATIONS

Yao, et al., "Transformer Fault Detection Based on Infrared Power Image," *Acta Technica* 62, 2A, Dec. 2017, pp. 237-244, Institute of Thermomechanics, Prague, Czech Republic.

Stannev, et al., "Some Shortcomings of the IEC 60214-1:2003 Standard, Regarding Type Tests of Tap-Changers and Drive Units," *18th International Symposium on Electrical Apparatus and Technologies*, May 29, 2014, pp. 1-4, Institute of Electrical and Electronics Engineers, Piscataway, NJ, USA.

Hoehlein-Atanasova, et al., "Carbon Oxides in the Interpretation of Dissolved Gas Analysis in Transformers and Tap Changers," *Electrical Insulation Magazine* 26, 6, Dec. 3, 2021, pp. 22-26, Institute of Electrical and Electronics Engineers, Piscataway, NJ, USA.

\* cited by examiner

MONITORING OF GASES PRODUCED IN AN INSULATING-MEANS CIRCUIT

CROSS REFERENCE TO RELATED APPLICATIONS

This application is a U.S. National Phase application under 35 U.S.C. § 371 of International Application No. PCT/EP2019/083870 (WO 2020/115232 A1), filed on Dec. 5, 2019, and claims benefit to German Patent Application No. DE 10 2018 131 388.8, filed on Dec. 7, 2018.

FIELD

The present invention relates to a method for monitoring gases produced in an insulating medium circuit, which is in contact with a transition resistor of an on-load tap-changer, and also to a corresponding on-load tap-changer.

BACKGROUND

The production of particular gases released in an insulating medium, for example an insulating oil in which an on-load tap-changer is located, such as in a transformer or another item of electrical equipment from the field of high-voltage technology for example, can be used as an indication of malfunctioning or imminent malfunctioning of the item of electrical equipment or of the on-load tap-changer. The prior art discloses methods which are concerned with state assessment and analysis of gases released in the insulating medium of high-voltage devices. In this case, the gases can be produced by the on-load tap-changer and/or other components of the item of equipment.

On-load tap-changers are used for changing over between winding taps of a transformer without interruption. Known on-load tap-changers usually consist of a selector for power-free selection of the respective winding tap of the transformer to which a changeover is intended to be made and a diverter switch for actually changing over from the previous winding tap to the new, preselected winding tap. The selector is usually accommodated in the insulating medium of the transformer and the diverter switch is usually accommodated in a separate insulating oil compartment in the transformer housing. However, the prior art likewise discloses securing the entire on-load tap-changer in the transformer housing without a separate compartment for the diverter switch, so that the diverter switch and the transformer are located in the same insulating medium circuit.

In known diverter switches in accordance with the high-speed resistor switching principle, transition resistors are used for limiting the load current during the intermittently simultaneous contact-connection of the currently connected-up winding tap and the preselected, new winding tap. During this process of diverter switch operation, the transition resistors are heated up and so-called hot gases, which are also to be expected with proper functioning of the on-load tap-changer, are produced.

Known methods and devices for monitoring gases produced in an insulating medium circuit and known methods for assessing the state of items of electrical equipment filled with insulating medium and having on-load tap-changers do not take into account, for example, the hot gases produced when the transition resistors are under stress and can therefore lead to incorrect interpretation of the gas analysis and have an adverse effect on the assessment of the state of the item of electrical equipment.

Separate or additional analysis of the gases produced by the on-load tap-changer is complex and costly. In the case of a common insulating medium circuit, separation of the gas components in accordance with responsible components of the item of equipment is not readily possible, and therefore such a separate analysis cannot be carried out.

SUMMARY

In an embodiment, the present disclosure provides a method that monitors gases produced in an insulating medium circuit. The insulating medium circuit is in contact with a transition resistor of an on-load tap-changer. The method includes: ascertaining a time profile of a resistor temperature of the transition resistor during a loading time period; and determining at least one characteristic value for characterizing the gases produced based upon the time profile of the resistor temperature.

BRIEF DESCRIPTION OF THE DRAWINGS

Subject matter of the present disclosure will be described in even greater detail below based on the exemplary figures. The invention defined by the following claims is not limited to the exemplary embodiments. All features described and/or illustrated herein can be used alone or combined in different combinations. The features and advantages of various embodiments will become apparent by reading the following detailed description with reference to the attached drawings, which illustrate the following:

DETAILED DESCRIPTION

Figure 1:
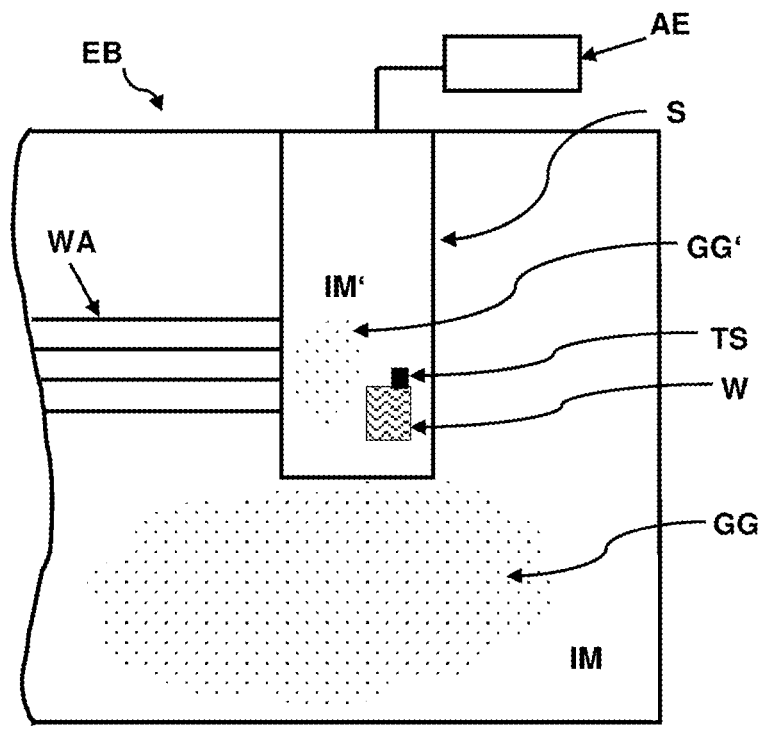
FIG. 1 shows a schematic design of an item of electrical equipment having an exemplary embodiment of an on-load tap-changer according to the improved concept.

Embodiments of the present invention provide an improved concept for monitoring gases produced in an insulating medium circuit having an on-load tap-changer, which allows gases produced by the on-load tap-changer to be taken into account in a simplified manner.

According to a first aspect of the improved concept of embodiments of the present invention, a method for monitoring gases produced in an insulating medium circuit is specified, wherein the insulating medium circuit is in contact with a transition resistor of an on-load tap-changer. In this case, a time profile of a resistor temperature of the transition resistor during a loading time period is ascertained, and at least one characteristic value for characterizing the gases produced is determined from the time profile of the resistor temperature.

Ascertaining the resistor temperature and the characteristic value that can be derived therefrom for characterizing the gases produced allows the gases—which are produced in the insulating medium of the on-load tap-changer, of a transformer or of another item of electrical equipment having the on-load tap-changer due to the transition resistors of the on-load tap-changer heating up-to be monitored; and therefore, allows a more accurate statement to be made about the state of the insulating medium, without having to make recourse to a dedicated gas analysis of the gases produced by the on-load tap-changer.

According to at least one embodiment, the on-load tap-changer is designed in accordance with the high-speed resistor switching principle.

According to at least one embodiment, the insulating medium is an insulating liquid, in particular insulating oil, for example a mineral transformer oil or an alternative insulating liquid, such as a synthetic ester for example.

According to at least one embodiment, the gases produced contain hydrogen, methane, ethane, ethene, propane or propene.

According to at least one embodiment, the loading time period of the transition resistor is, in particular, a time period in which a load current flows across the transition resistor and heats up said transition resistor.

According to at least one embodiment, the at least one characteristic value is determined on the basis of a curve of the time profile of the resistor temperature.

The curve represents, in particular, the function of the resistor temperature over time.

According to at least one embodiment, the characteristic value comprises a quantity of gas.

According to at least one embodiment of the method, the quantity of gas is ascertained by determining an area which is enclosed by the curve of the time profile of the resistor temperature.

The area may be, in particular, the entire area which is enclosed by the curve or only a portion of this area.

According to at least one embodiment, the area lies above a predetermined minimum temperature value.

The area can be determined, for example, by integration or approximate integration of the resistor temperature with respect to time.

The minimum temperature value is, in particular, characteristic of a temperature starting from which said hot gases are produced to a significant, in particular measurable, extent during operation of the on-load tap-changer. This value is, for example, dependent on the insulating medium used. For a mineral transformer oil, this value is, for example, approximately 100° C. The minimum temperature value is ascertained, for example, in advance by experiments.

According to at least one embodiment, the quantity of gas is compared with a defined limit value and a notification is output when the quantity of gas is equal to the defined limit value or exceeds the defined limit value.

In particular, the limit value is defined in such a way that the quantity of gas to be expected with proper functioning of the on-load tap-changer lies below this limit value. This is advantageous particularly when the on-load tap-changer and the transformer are located in a common insulating medium circuit. For example, the result of a gas analysis of the transformer oil is then not adversely affected to the effect that a fault is inferred on account of the quantity of gas present in the transformer oil even though the quantity of gas present can in no way be attributed to a malfunction of the transformer, but rather merely to the hot gases produced during the diverter switch operation.

According to at least one embodiment, the characteristic value comprises a gas composition.

According to at least one embodiment, the gas composition is ascertained using the curve of the time profile of the resistor temperature and a maximum resistor temperature.

In particular, the curve of the time profile of the resistor temperature represents the cooling-down behavior of the transition resistor after loading by a diverter switch operation.

For example, depending on the design and specific application, a transition resistor cools down from the maximum resistor temperature to an insulating medium temperature within 10-15 seconds after a diverter switch operation.

For example, the current, maximum resistor temperature can be determined in certain periods of time and the gas composition present given the respective temperatures, that is to say the type and quantity of gases released present in the insulating medium, can be ascertained by taking samples of insulating medium.

According to at least one embodiment, at least one lookup table can be created using these experiments, the lookup table containing information about which gases are produced at which resistor temperatures and therefore which gas composition is present in the insulating medium.

According to at least one embodiment, the curve of the time profile of the resistor temperature represents an exponential function or approximately an exponential function. In particular, the time profile of the resistor temperature can exponentially or approximately exponentially drop starting from the maximum resistor temperature.

According to at least one embodiment, ascertaining the resistor temperature comprises measuring the load current.

The load current of the transformer is measured, for example, by means of a current transformer.

According to at least one embodiment, the maximum resistor temperature can be calculated or approximated from the measured load current $I_L$, the temperature of the insulating medium $T_{IM}$ and application-specific design parameters of the on-load tap-changer, for example, as follows:

$$T_{max} = T_{IM} + \left(I_L^2 \times t_1 + \left(\frac{U_{St}}{R_{\ddot{u}}}\right)^2 \times t_2\right) \times \frac{0.271}{F^2}$$

where $$F = AnzPar \times \pi \times \frac{d^2}{4}$$

is the effective cross-sectional area of a transition resistor [mm$^2$].

The application-specific design parameters of the on-load tap-changer which are used in this formula are: the step voltage $U_{St}$, the size of the transition resistor $R_{\ddot{u}}$, the resistor loading times in respective tap-change steps $t_1$ and $t_2$, the number of parallel wires per resistor AnzPar and the wire diameter d.

According to at least one embodiment, ascertaining the resistor temperature comprises measuring the resistor temperature.

The resistor temperature can be measured directly and continuously during the loading time period or during a portion of the loading time period using, for example, a temperature sensor or a thermocouple on the transition resistor.

According to a second aspect of the improved concept, a method for assessing the state of an item of electrical equipment filled with insulating medium is also provided, wherein the item of equipment comprises an on-load tap-changer and the item of equipment and the on-load tap-changer have a common insulating medium circuit, and wherein the state assessment method comprises a method for monitoring gases produced according to the first aspect of the improved concept.

According to at least one embodiment, the item of electrical equipment is designed as a transformer.

According to at least one embodiment, the state assessment method comprises an analysis, in particular a gas analysis, for example an analysis of the composition and/or at least a concentration of gases released, of the insulating medium, wherein a result of the analysis is adapted depending on the at least one characteristic value.

For example, the result of a gas analysis of the transformer oil is adapted in such a way that the hot gases produced during operation of the on-load tap-changer are taken into account, for example removed by calculation, when assessing the state of the insulating medium.

According to the improved concept, an on-load tap-changer having a transition resistor is also provided, wherein the on-load tap-changer is designed in such a way that the transition resistor is in contact with an insulating medium circuit during operation of the on-load tap-changer. In this case, the on-load tap-changer has an evaluation device for monitoring gases produced in the insulating medium circuit, which evaluation device is designed to ascertain a profile of a resistor temperature of the transition resistor during a loading time period and to determine at least one characteristic value for characterizing the gases produced from the time profile of the resistor temperature.

According to at least one embodiment, the on-load tap-changer is designed in such a way that it can be installed in an item of electrical equipment, wherein the insulating medium circuit is a common insulating medium circuit of the item of equipment and the on-load tap-changer.

According to at least one embodiment, the on-load tap-changer does not have its own housing, but is arranged in a housing, for example tank or reservoir, of the item of electrical equipment.

According to at least one embodiment, the tap changer has an open housing and is arranged, with the open housing, in the housing of the item of electrical equipment.

According to at least one embodiment, the on-load tap-changer comprises a temperature sensor for measuring the resistor temperature.

Further embodiments of the on-load tap-changer according to the improved concept are evident directly from the various embodiments of the method according to the first and second aspect, and vice versa.

The present invention will be explained in detail below using exemplary embodiments with reference to the drawings. Components which are functionally identical or have an identical effect can be provided with identical reference signs. In some circumstances, identical components or components with an identical function are explained only with reference to the figure in which they appear for the first time. The explanation is not necessarily repeated in the following figures.

FIG. 1 shows an item of electrical equipment EB, for example a transformer, having a housing or tank which is at least partially filled with an insulating medium IM, for example transformer oil. Furthermore, an on-load tap-changer S is arranged in the housing of the item of electrical equipment, said on-load tap-changer likewise having a housing which is at least partially filled with insulating medium IM' and being connected to the winding taps WA of the transformer. A transition resistor W is arranged in the housing of the on-load tap-changer. However, the on-load tap-changer can also have a plurality of resistors. Different gases GG, GG' which are at least partially produced due to the resistors W being heated up may be present in dissolved form both in the insulating medium in the transformer housing and in the insulating medium in the on-load tap-changer housing. The on-load tap-changer has an evaluation device AE for monitoring the production of these hot gases.

The on-load tap-changer S optionally comprises a temperature sensor TS for measuring the resistor temperature. The temperature sensor TS is not required, for example, in those embodiments in which the resistor temperature is determined based on a measurement of the load current.

Figure 2:
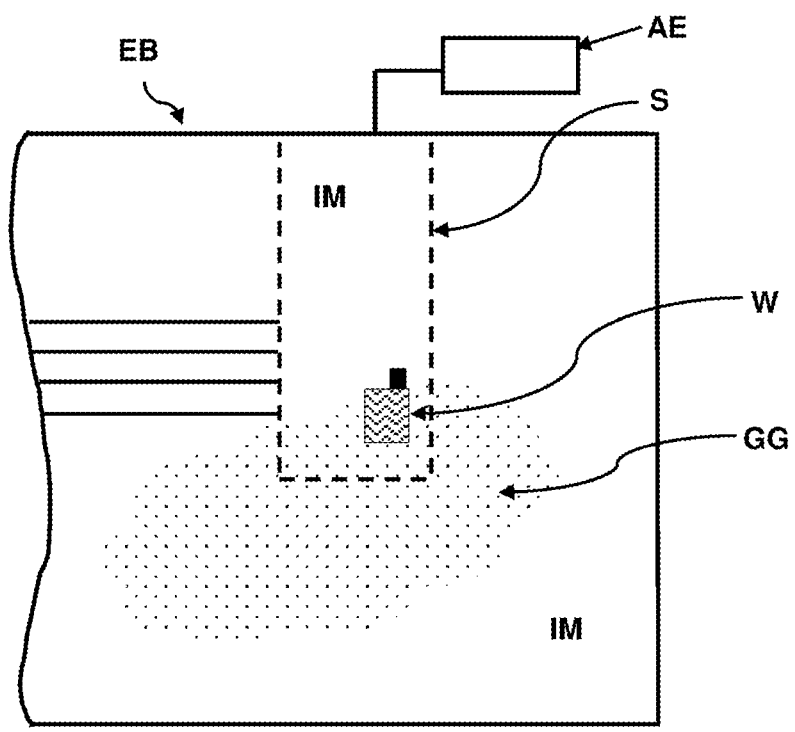
FIG. 2 shows a schematic design of a further item of equipment having a further exemplary embodiment of an on-load tap-changer according to the improved concept.

FIG. 2 schematically illustrates a further, exemplary embodiment of the improved concept, in which the item of electrical equipment EB and the on-load tap-changer S have a common insulating medium circuit IM with which the transition resistor W of the on-load tap-changer S is in contact. The on-load tap-changer S can have, for example, an open housing or even no housing at all, this being illustrated by the dashed line. Here, different gases GG released can also be present in the common insulating medium circuit IM, the gases being at least partially produced due to the transition resistor W being heated up.

Figure 3:
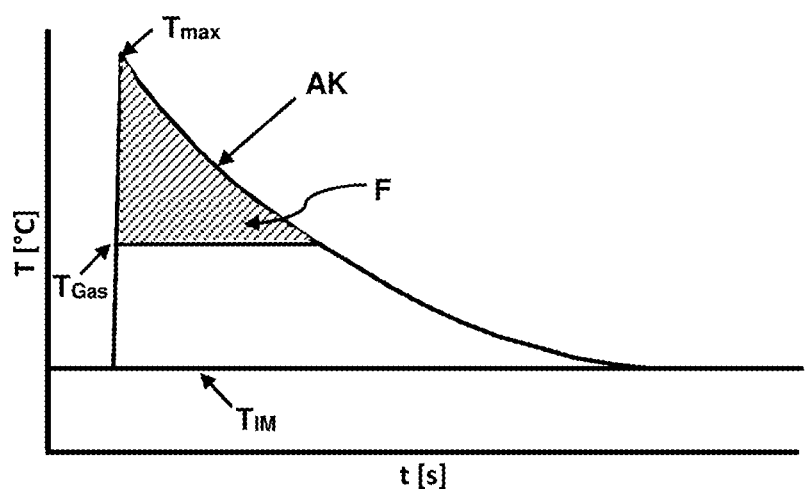
FIG. 3 shows an exemplary illustration of a curve of the time profile of a resistor temperature.

FIG. 3 shows an exemplary illustration of the resistor temperature T over time t during a tap-change process of the on-load tap-changer. The diagram contains a curve AK which represents the cooling-down behavior of a transition resistor during a diverter switch operation. With reference to the curve, it can be seen that the temperature is initially constant and equal to the temperature of the insulating medium $T_{IM}$. Then, during the course of the load current being diverted across the resistor, the resistor is significantly heated up to a maximum resistor temperature $T_{max}$ in a short time, followed by a slower, steady drop in the temperature back to the insulating medium temperature $T_{IM}$. The hatched area F depicts the region below the curve, which region is critical for the production of gas in the insulating medium. This region lies above a particular temperature $T_{Gas}$, for example 100° C., starting from which a significant quantity of hot gases can be produced and which can be ascertained by experiments. Therefore, firstly the time window in which the resistor cools completely back down to the insulating medium temperature after a diverter switch operation and secondly the time window in which said resistor is in a temperature range in which hot gases are produced can be ascertained using the cooling-down curve.

The quantity of gas produced can be ascertained using the size of the hatched area. That is to say, for example, the larger the area above $T_{Gas}$, the larger the quantity of gas produced in the insulating medium. In addition, a statement can be made about the gas composition, that is to say which type of gases are produced in the insulating medium, on the basis of the respective maximum temperature at the respective time.

A typical gas composition can be ascertained with continuous temperature measurement at the transition resistor, for example using a temperature sensor, by experiments for each period of time. The results can be compiled, for example, in a lookup table and used as an interpretation aid in future analyses.

While subject matter of the present disclosure has been illustrated and described in detail in the drawings and foregoing description, such illustration and description are to be considered illustrative or exemplary and not restrictive. It will be understood that changes and modifications may be made by those of ordinary skill within the scope of the following claims. In particular, the invention defined by the following claims may cover further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

REFERENCE SIGNS

EB Item of electrical equipment
S On-load tap-changer
WA Winding taps
AE Evaluation device
W Transition resistor
IM, IM' Insulating medium (circuit)
GG, GG' Gas released
TS Temperature sensor
AK (Cooling-down) curve
$T_{max}$ Maximum resistor temperature
$T_{Gas}$ Minimum temperature critical for gas production
$T_{IM}$ Insulating medium temperature
F Area

The invention claimed is:

1. A method for monitoring gases produced in an insulating medium circuit, wherein the insulating medium circuit is in contact with a transition resistor of an on-load tap-changer, the method comprising:
   ascertaining a time profile of a resistor temperature of the transition resistor during a loading time period; and
   determining at least one characteristic value for characterizing the gases produced based upon the time profile of the resistor temperature.

2. The method as claimed in claim 1, wherein the at least one characteristic value comprises a quantity of gas.

3. The method as claimed in claim 2, wherein the quantity of gas is ascertained by determining an area which is enclosed by a curve of the time profile of the resistor temperature.

4. The method as claimed in claim 3, wherein the area lies above a predetermined minimum temperature value.

5. The method as claimed in claim 2, the method comprising:
   comparing the quantity of gas with a defined limit value, and
   outputting a notification based upon determining that the quantity of gas is greater than or equal to a defined limit value.

6. The method as claimed in claim 1, wherein the at least one characteristic value comprises a gas composition.

7. The method as claimed in claim 6, wherein the gas composition is ascertained using a curve of the time profile of the resistor temperature and a maximum resistor temperature.

8. The method as claimed in claim 1, wherein ascertaining the resistor temperature comprises measuring a load current.

9. The method as claimed in claim 1, wherein ascertaining the resistor temperature comprises measuring the resistor temperature.

10. A method for assessing a state of an item of electrical equipment filled with the insulating medium, wherein the item of equipment comprises the on-load tap-changer, and the item of equipment and the on-load tap-changer have a common insulating medium circuit, and wherein:
    the state assessment method comprises the method for monitoring the gases produced as claimed in claim 1.

11. The method as claimed in claim 10, wherein:
    the state assessment method also comprises analysis of the insulating medium, and
    a result of the analysis is adapted depending on the at least one characteristic value.

12. An on-load tap-changer having a transition resistor, the on-load tap-changer configured that the transition resistor is in contact with an insulating medium circuit during operation of the on-load tap-changer, the on-load tap-changer having an evaluator configured to monitoring gases produced in the insulating medium circuit the evaluator being configured: to ascertain a profile of a resistor temperature of the transition resistor during a loading time period, and to determine at least one characteristic value for characterizing the gases produced from the time profile of the resistor temperature.

13. The on-load tap-changer as claimed in claim 12, wherein the on-load tap-changer is configured to be installed in an item of electrical equipment, wherein
    the insulating medium circuit is a common insulating medium circuit of the item of equipment and the on-load tap-changer.

14. The on-load tap-changer as claimed in claim 13, wherein the on-load tap-changer comprises a temperature sensor configured to measure the resistor temperature.

* * * * *